United States Patent
Gammie et al.

(10) Patent No.: US 9,681,864 B1
(45) Date of Patent: Jun. 20, 2017

(54) METHOD AND APPARATUS FOR TRANSAPICAL PROCEDURES ON A MITRAL VALVE

(71) Applicants: Harpoon Medical, Inc., Baltimore, MD (US); University of Maryland, Baltimore, MD (US)

(72) Inventors: James Gammie, Stevenson, MD (US); Peter Wilson, Killingworth, CT (US); Peter Boyd, San Francisco, CA (US); William Niland, Arnold, MD (US)

(73) Assignees: Harpoon Medical, Inc., Baltimore, MD (US); University of Maryland, Baltimore, Baltimore, MD (US)

( * ) Notice: Subject to any disclaimer, the term of this patent is extended or adjusted under 35 U.S.C. 154(b) by 121 days.

(21) Appl. No.: 14/584,561

(22) Filed: Dec. 29, 2014

Related U.S. Application Data

(60) Provisional application No. 61/923,359, filed on Jan. 3, 2014.

(51) Int. Cl.
*A61F 2/24* (2006.01)
*A61B 17/04* (2006.01)
*A61B 17/06* (2006.01)

(52) U.S. Cl.
CPC .... *A61B 17/0401* (2013.01); *A61B 17/06166* (2013.01); *A61B 2017/0445* (2013.01); *A61B 2017/0458* (2013.01)

(58) Field of Classification Search
CPC ...... A61B 2017/00243; A61B 17/0401; A61B 2017/0409; A61B 17/0469;
(Continued)

(56) References Cited

U.S. PATENT DOCUMENTS

| 3,131,957 A | 5/1964 | Musto |
| 3,752,516 A | 8/1973 | Mumma |

(Continued)

FOREIGN PATENT DOCUMENTS

| EP | 0791330 | 6/2005 |
| WO | WO 2006/078694 | 7/2006 |

(Continued)

OTHER PUBLICATIONS

Office Action for U.S. Appl. No. 11/683,282, mailed Feb. 27, 2009, 6 pages.

(Continued)

*Primary Examiner* — Katherine M Shi
(74) *Attorney, Agent, or Firm* — Cooley LLP

(57) ABSTRACT

Apparatus and methods for performing a non-invasive procedure to repair a cardiac valve are described herein. In some embodiments, apparatus and methods are described herein for repairing a mitral valve using an edge-to-edge repair to secure the mitral valve leaflets. Implant securing devices are also described that can be used during a procedure to repair a mitral valve. In some embodiments, an implant securing device includes an outer member and an inner member movably disposed within the outer member. The inner member can be used to hold or secure a suture extending from an implant deployed on an atrial side of a leaflet of a mitral valve, and the outer member can be used to push or move a half hitch knot toward a ventricular side of the leaflet, which can be used to secure the implant in the desired position.

16 Claims, 13 Drawing Sheets

(58) Field of Classification Search
CPC .. A61B 2017/0496; A61B 2017/00783; A61B 17/00234; A61B 2017/0406; A61F 2/2466; A61F 2/2445; A61F 2/2457; A61F 2/2418; A61F 2/2412; A61F 2220/0016; A61F 2/2409; A61F 2/2427; A61F 2250/001; A61F 2210/0014; A61F 2/2442; A61F 2/2454; A61F 2/246; A61F 2220/00
USPC ...... 623/2.11, 2.36, 2.37, 2.4; 606/139, 144, 606/145, 228, 232
See application file for complete search history.

(56) References Cited

U.S. PATENT DOCUMENTS

| | | |
|---|---|---|
| 4,403,797 A | 9/1983 | Ragland, Jr. |
| 5,144,961 A | 9/1992 | Chen et al. |
| 5,147,316 A | 9/1992 | Castillenti |
| 5,312,423 A | 5/1994 | Rosenbluth et al. |
| 5,391,176 A | 2/1995 | de la Torre |
| 5,405,352 A | 4/1995 | Weston |
| 5,454,821 A | 10/1995 | Harm et al. |
| 5,472,446 A | 12/1995 | de la Torre |
| 5,507,754 A | 4/1996 | Green et al. |
| 5,527,323 A | 6/1996 | Jervis et al. |
| 5,554,184 A | 9/1996 | Machiraju |
| 5,626,614 A | 5/1997 | Hart |
| 5,643,293 A | 7/1997 | Kogasaka et al. |
| 5,681,331 A | 10/1997 | de la Torre et al. |
| 5,716,368 A | 2/1998 | de la Torre et al. |
| 5,727,569 A | 3/1998 | Benetti et al. |
| 5,728,109 A | 3/1998 | Schulze et al. |
| 5,746,752 A | 5/1998 | Burkhart |
| 5,769,862 A | 6/1998 | Kammerer et al. |
| 5,797,928 A | 8/1998 | Kogasaka |
| 5,824,065 A | 10/1998 | Gross |
| 5,931,868 A | 8/1999 | Gross |
| 5,957,936 A | 9/1999 | Yoon et al. |
| 5,971,447 A | 10/1999 | Steck, III |
| 6,010,531 A | 1/2000 | Donlon et al. |
| 6,074,417 A | 6/2000 | Peredo |
| 6,269,819 B1 | 8/2001 | Oz et al. |
| 6,332,893 B1 | 12/2001 | Mortier et al. |
| 6,562,051 B1 | 5/2003 | Bolduc et al. |
| 6,626,930 B1 | 9/2003 | Allen et al. |
| 6,629,534 B1 | 10/2003 | St. Goar et al. |
| 6,840,246 B2 | 1/2005 | Downing |
| 6,921,408 B2 | 7/2005 | Sauer |
| 6,978,176 B2 | 12/2005 | Lattouf |
| 6,991,635 B2 | 1/2006 | Takamoto et al. |
| 6,997,950 B2 | 2/2006 | Chawla |
| 7,112,207 B2 | 9/2006 | Allen et al. |
| 7,291,168 B2 | 11/2007 | Macoviak et al. |
| 7,294,148 B2 | 11/2007 | McCarthy |
| 7,309,086 B2 | 12/2007 | Carrier |
| 7,316,706 B2 | 1/2008 | Bloom et al. |
| 7,373,207 B2 | 5/2008 | Lattouf |
| 7,431,692 B2 | 10/2008 | Zollinger et al. |
| 7,513,908 B2 | 4/2009 | Lattouf |
| 7,534,260 B2 | 5/2009 | Lattouf |
| 7,608,091 B2 | 10/2009 | Goldfarb et al. |
| 7,618,449 B2 | 11/2009 | Tremulis et al. |
| 7,632,308 B2 | 12/2009 | Loulmet |
| 7,635,386 B1 | 12/2009 | Gammie |
| 7,666,196 B1 | 2/2010 | Miles |
| 7,744,609 B2 | 6/2010 | Allen et al. |
| 7,837,727 B2 | 11/2010 | Goetz |
| 7,871,368 B2 | 1/2011 | Zollinger et al. |
| 7,871,433 B2 | 1/2011 | Lattouf |
| 7,959,650 B2 | 6/2011 | Kaiser et al. |
| 8,029,518 B2 | 10/2011 | Goldfarb et al. |
| 8,029,565 B2 | 10/2011 | Lattouf |
| 8,043,368 B2 | 10/2011 | Crabtree |
| 8,147,542 B2 | 4/2012 | Maisano et al. |
| 8,187,323 B2 | 5/2012 | Mortier et al. |
| 8,226,711 B2 | 7/2012 | Mortier et al. |
| 8,241,304 B2 | 8/2012 | Bachman |
| 8,252,050 B2 | 8/2012 | Maisano et al. |
| 8,292,884 B2 | 10/2012 | Levine et al. |
| 8,303,622 B2 | 11/2012 | Alkhatib |
| 8,333,788 B2 | 12/2012 | Maiorino |
| 8,382,829 B1 | 2/2013 | Call et al. |
| 8,439,969 B2 | 5/2013 | Gillinov et al. |
| 8,454,656 B2 | 6/2013 | Tuval |
| 8,465,500 B2 | 6/2013 | Speziali |
| 8,475,525 B2 | 7/2013 | Maisano et al. |
| 8,500,800 B2 | 8/2013 | Maisano et al. |
| 8,608,758 B2 | 12/2013 | Singhatat et al. |
| 8,663,278 B2 | 3/2014 | Mabuchi et al. |
| 8,771,296 B2 | 7/2014 | Nobles et al. |
| 8,828,053 B2 | 9/2014 | Sengun et al. |
| 8,852,213 B2 | 10/2014 | Gammie et al. |
| 9,131,884 B2 | 9/2015 | Holmes et al. |
| 2002/0013571 A1 | 1/2002 | Goldfarb et al. |
| 2003/0023254 A1 | 1/2003 | Chiu |
| 2003/0094180 A1 | 5/2003 | Benetti |
| 2003/0105519 A1 | 6/2003 | Fasol et al. |
| 2003/0120264 A1 | 6/2003 | Lattouf |
| 2003/0120341 A1 | 6/2003 | Shennib et al. |
| 2004/0044365 A1 | 3/2004 | Bachman |
| 2004/0093023 A1 | 5/2004 | Allen et al. |
| 2004/0143323 A1 | 7/2004 | Chawla |
| 2004/0199183 A1 | 10/2004 | Oz et al. |
| 2005/0004667 A1 | 1/2005 | Swinford et al. |
| 2005/0075654 A1 | 4/2005 | Kelleher |
| 2005/0119735 A1 | 6/2005 | Spence et al. |
| 2005/0149067 A1 | 7/2005 | Takemoto et al. |
| 2005/0149093 A1 | 7/2005 | Pokorney |
| 2005/0154402 A1 | 7/2005 | Sauer et al. |
| 2005/0216036 A1 | 9/2005 | Nakao |
| 2005/0216077 A1 | 9/2005 | Mathis et al. |
| 2005/0267493 A1 | 12/2005 | Schreck et al. |
| 2006/0100698 A1 | 5/2006 | Lattouf |
| 2006/0111739 A1 | 5/2006 | Staufer |
| 2006/0167541 A1 | 7/2006 | Lattouf |
| 2006/0190030 A1 | 8/2006 | To et al. |
| 2007/0010857 A1 | 1/2007 | Sugimoto et al. |
| 2007/0049952 A1 | 3/2007 | Weiss |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0149995 A1 | 6/2007 | Quinn et al. |
| 2007/0197858 A1 | 8/2007 | Goldfarb et al. |
| 2007/0213582 A1 | 9/2007 | Zollinger et al. |
| 2007/0270793 A1 | 11/2007 | Lattouf |
| 2008/0004597 A1 | 1/2008 | Lattouf et al. |
| 2008/0009888 A1 | 1/2008 | Ewers et al. |
| 2008/0065203 A1 | 3/2008 | Khalapyan |
| 2008/0140093 A1 | 6/2008 | Stone et al. |
| 2008/0167714 A1 | 7/2008 | St. Goar et al. |
| 2008/0188893 A1 | 8/2008 | Selvitelli et al. |
| 2008/0228223 A1 | 9/2008 | Alkhatib |
| 2008/0249504 A1 | 10/2008 | Lattouf et al. |
| 2008/0269781 A1 | 10/2008 | Funamura et al. |
| 2009/0005863 A1 | 1/2009 | Goetz et al. |
| 2009/0043153 A1 | 2/2009 | Zollinger et al. |
| 2009/0105729 A1 | 4/2009 | Zentgraf |
| 2009/0105751 A1 | 4/2009 | Zentgraf |
| 2009/0276038 A1 | 11/2009 | Tremulis et al. |
| 2010/0023056 A1 | 1/2010 | Johansson et al. |
| 2010/0023117 A1 | 1/2010 | Yoganathan et al. |
| 2010/0023118 A1 | 1/2010 | Medlock |
| 2010/0042147 A1 | 2/2010 | Janovsky et al. |
| 2010/0174297 A1 | 7/2010 | Speziali |
| 2010/0179574 A1 | 7/2010 | Longoria et al. |
| 2010/0210899 A1 | 8/2010 | Schankereli |
| 2010/0298930 A1 | 11/2010 | Orlov |
| 2011/0015476 A1 | 1/2011 | Franco |
| 2011/0022083 A1 | 1/2011 | DiMatteo et al. |
| 2011/0022084 A1 | 1/2011 | Sengun et al. |
| 2011/0028995 A1 | 2/2011 | Miraki et al. |
| 2011/0029071 A1 | 2/2011 | Zlotnick et al. |
| 2011/0060407 A1 | 3/2011 | Ketai et al. |

(56) References Cited

U.S. PATENT DOCUMENTS

| | | |
|---|---|---|
| 2011/0106106 A1 | 5/2011 | Meier |
| 2011/0144743 A1 | 6/2011 | Lattouf |
| 2011/0264208 A1 | 10/2011 | Duffy et al. |
| 2011/0270278 A1 | 11/2011 | Overes et al. |
| 2011/0288637 A1 | 11/2011 | De Marchena |
| 2012/0004669 A1 | 1/2012 | Overes et al. |
| 2012/0143215 A1 | 6/2012 | Carrao et al. |
| 2012/0150223 A1 | 6/2012 | Manos et al. |
| 2012/0179184 A1 | 7/2012 | Orlov |
| 2012/0184971 A1 | 7/2012 | Zentgraf et al. |
| 2012/0203072 A1 | 8/2012 | Lattouf et al. |
| 2012/0226294 A1 | 9/2012 | Tuval |
| 2012/0226349 A1 | 9/2012 | Tuval et al. |
| 2013/0018459 A1 | 1/2013 | Maisano et al. |
| 2013/0035757 A1 | 2/2013 | Zentgraf et al. |
| 2013/0253641 A1 | 9/2013 | Lattouf |
| 2013/0282059 A1 | 10/2013 | Ketai et al. |
| 2013/0345749 A1 | 12/2013 | Sullivan et al. |
| 2014/0031926 A1 | 1/2014 | Kudlik et al. |
| 2014/0039607 A1 | 2/2014 | Kovach |
| 2014/0067052 A1 | 3/2014 | Chau et al. |
| 2014/0114404 A1 | 4/2014 | Gammie et al. |
| 2014/0214152 A1 | 7/2014 | Bielefeld |
| 2014/0243968 A1 | 8/2014 | Padala |
| 2014/0364938 A1 | 12/2014 | Longoria et al. |
| 2015/0032127 A1 | 1/2015 | Gammie et al. |
| 2015/0045879 A1 | 2/2015 | Longoria et al. |

FOREIGN PATENT DOCUMENTS

| | | |
|---|---|---|
| WO | WO 2007/100268 | 9/2007 |
| WO | WO 2008/013869 | 1/2008 |
| WO | WO 2008/124110 | 10/2008 |
| WO | WO 2008/143740 | 11/2008 |
| WO | WO 2009/081396 | 7/2009 |
| WO | WO 2010/070649 | 6/2010 |
| WO | WO 2010/105046 | 9/2010 |
| WO | WO 2012/137208 | 10/2012 |
| WO | WO 2013/003228 | 1/2013 |
| WO | WO 2014/093861 | 6/2014 |
| WO | WO 2015/020816 | 2/2015 |

OTHER PUBLICATIONS

Supplementary European Search Report for European Application No. 12804880.8, mailed Nov. 28, 2014, 6 pages.
Office Action for U.S. Appl. No. 14/138,857, mailed May 5, 2014, 12 pages.
Office Action for U.S. Appl. No. 14/478,325, mailed Nov. 18, 2014, 9 pages.
Final Office Action for U.S. Appl. No. 14/478,325, mailed May 15, 2015, 15 pages.
Office Action for U.S. Appl. No. 14/478,325, mailed Mar. 4, 2016, 15 pages.
Final Office Action for U.S. Appl. No. 14/478,325, mailed Aug. 17, 2016.
International Search Report for International Application No. PCT/US2012/043761, mailed Dec. 3, 2012.
International Preliminary Report on Patentability for International Application No. PCT/US2012/043761, mailed Jan. 16, 2014.
Alfieri, O. et al., "The double-orifice technique in mitral valve repair: a simple solution for complex problems," (2001) J. Thorac. Cardiovasc. Surg., 122(4):674-681.
Barbero-Marcial, M. et al., "Transxiphoid Approach Without Median Sternotomy for the Repair of Atrial Septal Defects," (1998) Ann. Thorac. Surg., 65(3):771-774.
Braunberger, E. et al., "Very long-term results (more than 20 years) of valve repair with Carpentier's techniques in nonheumatic mitral valve insufficiency," (2001) Circulation, 104:I-8-I-11.
Carpentier, Alain, "Cardiac valve surgery—the 'French correction'," The Journal of Thoracic and Cardiovascular Surgery, vol. 86, No. 3, Sep. 1983, 15 pages.

David, T. E. et al., "Replacement of chordae tendineae with Gore-Tex sutures: a ten-year experience," (1996) J. Heart Valve Dis., 5(4):352-355.
David, T. E. et al., "Mitral valve repair by replacement of chordae tendineae with polytetrafluoroethylene sutures," (1991) J. Thorac. Cardiovasc. Surg., 101(3):495-501.
Doty, D. B. et al., "Full-Spectrum Cardiac Surgery Through a Minimal Incision: Mini-Sternotomy (Lower Half) Technique," (1998) Ann. Thorac. Surg., 65(2):573-577.
Duran, C. M. G. et al., "Techniques for ensuring the correct length of new mitral chords," (2003) J. Heart Valve Dis., 12(2):156-161.
Eishi, K. et al., "Long-term results of artificial chordae implantation in patients with mitral valve prolapse," (1997) J. Heart Valve Dis., 6(6):594-598.
Frater, R. W. M., "Anatomical rules for the plastic repair of a diseased mitral valve," (1964) Thorax, 19:458-464.
Frater, R. W. M. et al., "Chordal replacement in mitral valve repair," (1990) Circulation, 82(suppl. IV):IV-125-IV-130.
Huber, C. H. et al., "Direct Access Valve Replacement (DAVR)—are we entering a new era in cardiac surgery?" (2006) European Journal of Cardio-thoracic Surgery, 29:380-385.
Hvass, U. et al., "Papillary Muscle Sling: A New Functional Approach to Mitral Repair in Patients With Ischemic Left Ventricular Dysfunction and Functional Mitral Regurgitation," (2003) Ann. Thorac. Surg., 75:809-811.
Kasegawa, H. et al., "Simple method for determining proper length of artificial chordae in mitral valve repair," (1994) Ann. Thorac. Surg., 57(1):237-239.
Kobayashi, J. et al., "Ten-year experience of chordal replacement with expanded polytetrafluoroethylene in mitral valve repair," (2000) Circulation, 102(19 Suppl 3):Iii-30-Iii-34.
Kunzelman, K. et al., "Replacement of mitral valve posterior chordae tendineae with expanded polytetrafluoroethylene suture: a finite element study," (1996) J. Card. Surg., 11(2):136-145.
Langer, F. et al., "RING plus STRING: Papillary muscle repositioning as an adjunctive repair technique for ischemic mitral regurgitation," (2007) J. Thorac. Cardiovasc. Surg., 133(1): 247-249.
Maisano, F. et al., "The double-orifice technique as a standardized approach to treat mitral regurgitation due to severe myxomatous disease: surgical technique," (2000) European Journal of Cardio-thoracic Surgery, 17(3):201-205.
Merendino, K. A. et al., "The open correction of rheumatic mitral regurgitation and/or stenosis with special reference to regurgitation treated by posteromedial annuloplasty utilizing a pump-oxygenator," (1959) Annals of Surgery, 150(1):5-22.
Minatoya, K. et al., "Pathologic aspects of polytetrafluoroethylene sutures in human heart," (1996) Ann. Thorac. Surg., 61(3):883-887.
Mohty, D. et al., "Very long-term survival and durability of mitral valve repair for mitral valve prolapse," (2001) Circulation, 104:I-1-I-7.
*Neochord, Inc.* v. *University of Maryland, Baltimore*, Case No. IPR2016-00208, Petition for *Inter Partes*Review of U.S. Pat. No. 7,635,386, dated Nov. 18, 2015, 65 pages.
*Neochord, Inc.* v. *University of Maryland, Baltimore*, Case No. IPR2016-00208, Declaration of Dr. Lishan Aklog, dated Nov. 17, 2015, 91 pages.
*Neochord, Inc.* v. *University of Maryland, Baltimore*, Case No. IPR2016-00208, Decision on Institution of *Inter Partes Review*,37 CFR §42.108, Paper 6, Entered May 24, 2016, 28 pages.
Nigro, J. J. et al., "Neochordal repair of the posterior mitral leaflet," (2004) J. Thorac. Cardiovasc. Surg., 127(2):440-447.
Phillips, M. R. et al., "Repair of anterior leaflet mitral valve prolapse: chordal replacement versus chordal shmtening," (2000) Ann. Thorac. Surg., 69(1):25-29.
Russo, M. J. et al. "Transapical Approach for Mitral Valve Repair during Insertion of a Left Ventricular Assist Device," Hindawi Publishing Corporation, The Scientific World Journal, vol. 2013, Article ID 925310, [online], Retrieved from the Internet: <URL: http://dx.doi.org/10.1155/2013/925310> Apr. 11, 2013, 4 pages.
Sarsam, M. A. I., "Simplified technique for determining the length of artificial chordae in mitral valve repair," (2002) Ann. Thorac. Surg., 73(5):1659-1660.

(56) References Cited

OTHER PUBLICATIONS

Savage, E. B. et al., "Use of mitral valve repair: analysis of contemporary United States experience reported to the society of thoracic surgeons national cardiac database," (2003) Ann. Thorac. Surg., 75:820-825.

Speziali, G. et al., "Correction of Mitral Valve Regurgitation by Off-Pump, Transapical Placement of Artificial Chordae Tendinae, Results of the European TACT Trial," AATS 93rd Annual Meeting 2013, www.aats.org, 26 pages.

Suematsu, Y. et al., "Three-dimensional echo-guided beating heart surgery without cardiopulmonary bypass: Atrial septal defect closure in a swine model," (2005) J. Thorac. Cardiovasc. Surg., 130:1348-1357.

von Oppell, U. O. et al., "Chordal replacement for both minimally invasive and conventional mitral valve surgery using premeasured Gore-Tex loops," (2000) Ann. Thorac. Surg., 70(6):2166-2168.

Zussa, C., "Artificial chordae," (1995) J. Heart Valve Dis., 4(2):S249-S256.

Zussa, C. et al., "Artificial mitral valve chordae: experimental and clinical experience," (1990) Ann. Thorac. Surg., 50(3):367-373.

Zussa, C. et al., "Seven-year experience with chordal replacement with expanded polytetrafluoroethylene in floppy mitral valve," (1994) J. Thorac. Cardiovasc. Surg., 108(1):37-41.

Zussa, C. et al., "Surgical technique for artificial mitral chordae implantation," (1991) Journal of Cardiac Surgery, 6(4):432-438.

*Neochord, Inc.* v. *University of Maryland, Baltimore*, Case No. IPR2016-00208, Patent Owner's Response Under 37 C.F.R. § 42.120, with Exhibits 1001-1011, filed Sep. 12, 2016, 299 pages.

*Neochord, Inc.* v. *University of Maryland, Baltimore*, Case No. IPR2016-00208, Reply to Patent Owner's Response, with Exhibits 1012-1014, filed Nov. 28, 2016, 83 pages.

Advisory Action for U.S. Appl. No. 14/478,325, mailed Nov. 4, 2016, 4 pages.

Notice of Panel Decision from Pre-Appeal Brief Review for U.S. Appl. No. 14/478,325, mailed Dec. 16, 2016, 2 pages.

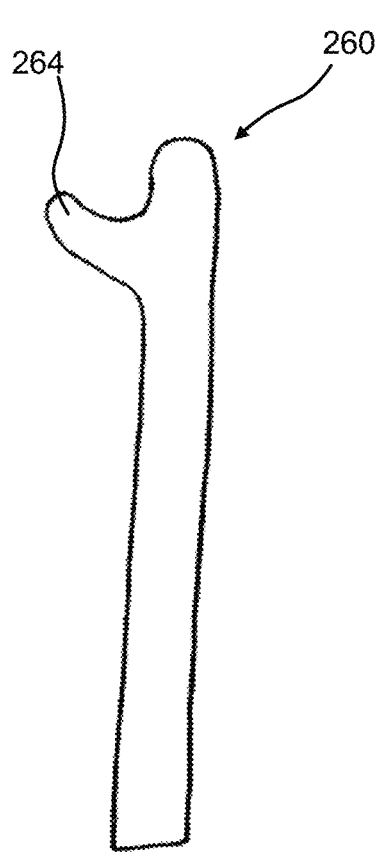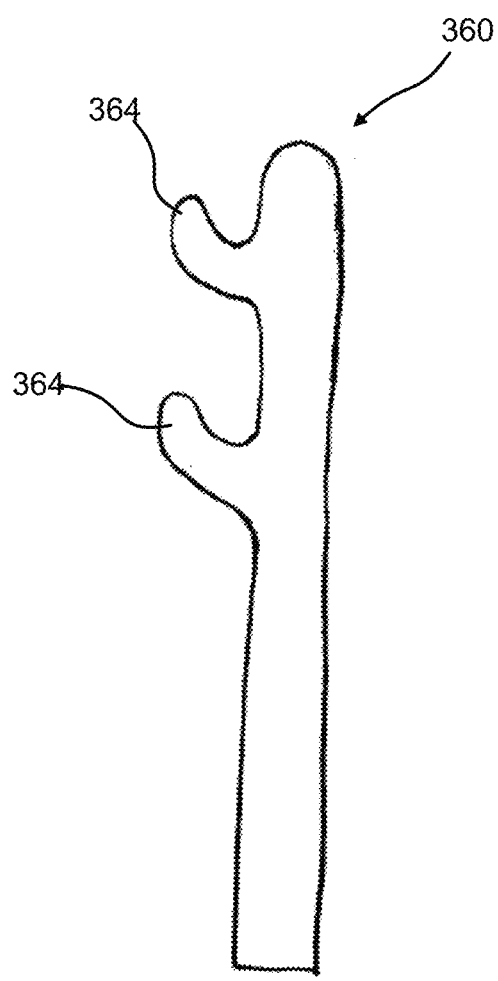
FIG. 13
FIG. 14

METHOD AND APPARATUS FOR TRANSAPICAL PROCEDURES ON A MITRAL VALVE

CROSS-REFERENCE TO RELATED APPLICATIONS

This applications claims priority to and the benefit from U.S. Provisional Application Ser. No. 61/923,359, entitled "Method and Apparatus for Transapical Procedures on a Mitral Valve," filed Jan. 3, 2014, the disclosure of which is incorporated herein by reference in its entirety.

BACKGROUND

Some embodiments described herein relate to methods and apparatus for performing cardiac valve repairs, and more particularly, methods and apparatus for performing minimally invasive mitral or tricuspid valve repairs.

Various disease processes can impair the proper functioning of one or more of the valves of the heart. These disease processes include degenerative processes (e.g., Barlow's Disease, fibroelastic deficiency), inflammatory processes (e.g., Rheumatic Heart Disease), and infectious processes (e.g., endocarditis). Additionally, damage to the ventricle from prior heart attacks (i.e., myocardial infarction secondary to coronary artery disease) or other heart diseases (e.g., cardiomyopathy) can distort the valve's geometry causing it to dysfunction.

Mitral valve regurgitation occurs when the leaflets of the valve do not close completely thereby causing blood to leak back into the prior chamber. There are three mechanisms by which a valve becomes regurgitant or incompetent. The three mechanisms include Carpentier's type I, type II and type III malfunctions. A Carpentier type I malfunction involves the dilation of the annulus such that normally functioning leaflets are distracted from each other and fail to form a tight seal (i.e., do not coapt properly). Included in a type I mechanism malfunction are perforations of the valve leaflets, as in endocarditis. A Carpentier's type II malfunction involves prolapse of one or both leaflets above the plane of coaptation. This is the most common cause of mitral regurgitation, and is often caused by the stretching or rupturing of chordae tendineae normally connected to the leaflet. A Carpentier's type III malfunction involves restriction of the motion of one or more leaflets such that the leaflets are abnormally constrained below the level of the plane of the annulus. Leaflet restriction can be caused by rheumatic disease (IIIa) or dilation of the ventricle (IIIb).

Mitral valve disease is the most common valvular heart disorder, with nearly 4 million Americans estimated to have moderate to severe mitral valve regurgitation ("MR"). MR results in a volume overload on the left ventricle which in turn progresses to ventricular dilation, decreased ejection performance, pulmonary hypertension, symptomatic congestive heart failure, atrial fibrillation, right ventricular dysfunction and death. Successful surgical mitral valve repair restores mitral valve competence, abolishes the volume overload on the left ventricle, improves symptom status and prevents adverse left ventricular remodeling.

Malfunctioning valves may either be repaired or replaced. Repair typically involves the preservation and correction of the patient's own valve. Replacement typically involves replacing the patient's malfunctioning valve with a biological or mechanical substitute. Typically, replacement is preferred for stenotic damage sustained by the leaflets because the stenosis is irreversible. The mitral valve and tricuspid valve, on the other hand, are more prone to deformation. Deformation of the leaflets, as described above, prevents the valves from closing properly and allows for regurgitation or back flow from the ventricle into the atrium, which results in valvular insufficiency. Deformations in the structure or shape of the mitral valve or tricuspid valve are often repairable.

In mitral valve regurgitation, repair is preferable to valve replacement. Bioprosthetic valves have limited durability. Moreover, prosthetic valves rarely function as well as the patient's own valves. Additionally, there is an increased rate of survival and a decreased mortality rate and incidence of endocarditis for repair procedures. Further, because of the risk of thromboembolism, mechanical valves often require further maintenance, such as the lifelong treatment with blood thinners and anticoagulants. Therefore, an improperly functioning mitral valve or tricuspid valve is ideally repaired, rather than replaced. However, because of the complex and technical demands of the repair procedures, the mitral valve is still replaced in approximately one third of all mitral valve operations performed in the United States.

Carpentier type I malfunction, sometimes referred to as "Functional MR," is associated with heart failure and affects between 1.6 and 2.8 million people in the United States alone. Studies have shown that mortality doubles in patients with untreated mitral valve regurgitation after myocardial infarction. Unfortunately, there is no gold standard surgical treatment paradigm for functional MR and most functional MR patients are not referred for surgical intervention due to the significant morbidity, risk of complications and prolonged disability associated with cardiac surgery. Surgeons use a variety of approaches ranging from valve replacement to insertion of an undersized mitral valve annuloplasty ring for patients suffering from functional MR and the long term efficacy is still unclear. Dr. Alfieri has demonstrated the benefit of securing the midpoint of both leaflets together creating a double orifice valve in patients with MR known as an "Edge-to-Edge" repair or an Alfieri procedure.

Regardless of whether a replacement or repair procedure is being performed, conventional approaches for replacing or repairing cardiac valves are typically invasive open-heart surgical procedures, such as sternotomy or thoracotomy, which require opening up of the thoracic cavity so as to gain access to the heart. Once the chest has been opened, the heart is bypassed and stopped. Cardiopulmonary bypass is typically established by inserting cannulae into the superior and inferior vena cavae (for venous drainage) and the ascending aorta (for arterial perfusion), and connecting the cannulae to a heart-lung machine, which functions to oxygenate the venous blood and pump it into the arterial circulation, thereby bypassing the heart. Once cardiopulmonary bypass has been achieved, cardiac standstill is established by clamping the aorta and delivering a "cardioplegia" solution into the aortic root and then into the coronary circulation, which stops the heart from beating. Once cardiac standstill has been achieved, the surgical procedure may be performed. These procedures, however, adversely affect almost all of the organ systems of the body and may lead to complications, such as strokes, myocardial "stunning" or damage, respiratory failure, kidney failure, bleeding, generalized inflammation, and death. The risk of these complications is directly related to the amount of time the heart is stopped ("cross-clamp time") and the amount of time the subject is on the heart-lung machine ("pump time").

Thus there is a significant need to perform mitral valve repairs using less invasive procedures while the heart is still beating. Accordingly, there is a continuing need for new procedures and devices for performing cardiac valve repairs, such as mitral valve repair, which are less invasive, do not require cardiac arrest, and are less labor-intensive and technically challenging.

SUMMARY

Apparatus and methods for performing a non-invasive procedure to repair a cardiac valve are described herein. In some embodiments, apparatus and methods are described herein for repairing a mitral valve using an edge-to-edge procedure (also referred to as an Alfieri procedure) to secure the mitral valve leaflets. Implant securing devices are also described that can be used during a procedure to repair a mitral valve. In some embodiments, an implant securing device includes an outer member and an inner member movably disposed within the outer member. The inner member can be used to hold or secure a suture extending from an implant deployed on an atrial side of a leaflet of a mitral valve, and the outer member can be used to push or move a knot, such as a half-hitch, toward a ventricular side of the leaflet, which can be used to secure the implant in a desired position.

BRIEF DESCRIPTION OF THE DRAWINGS

FIG. 13 is a side view of a portion of a pusher device, according to another embodiment.

FIG. 14 is a side view of a portion of a pusher device, according to yet another embodiment.

DETAILED DESCRIPTION

Apparatus and methods for performing a non-invasive procedure to repair a cardiac valve are described herein. In some embodiments, apparatus and methods are described herein for performing a non-invasive procedure for repairing a mitral valve using an edge-to-edge stitch (also referred to as an Alfieri procedure) to secure an implant to the mitral valve leaflets.

Figure 1:
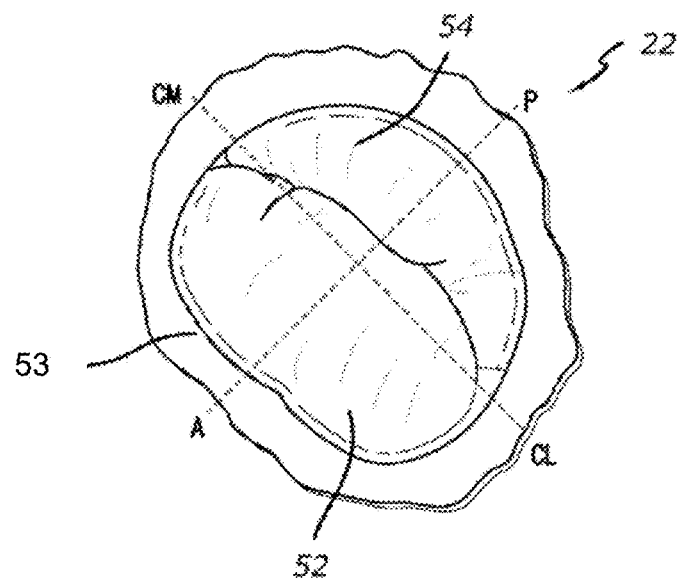
FIG. 1 is a top perspective view of a healthy mitral valve with the mitral leaflets closed.

As illustrated in FIG. 1, the mitral valve 22 includes two leaflets, the anterior leaflet 52 and the posterior leaflet 54, and a diaphanous incomplete ring around the valve, called the annulus 53. The mitral valve 22 has two papillary muscles, the anteromedial and the posterolateral papillary muscles (not shown), which attach the leaflets 52, 54 to the walls of the left ventricle (not shown) via the chordae tendineae (not shown). The mitral valve 22, also referred to as the left atrioventricular valve, controls the passage of oxygenated blood from the left atrium (not shown) of the heart to the left ventricle (not shown). The mitral valve 22 is part of the "left" heart, which controls the flow of oxygen-rich blood from the lungs to the body. The mitral valve 22 lies between a receiving chamber (atrium) and a ventricle so as to control the flow of blood from the atria to the ventricles and prevent blood from leaking back into the atrium during ejection into the ventricle.

Figure 2:
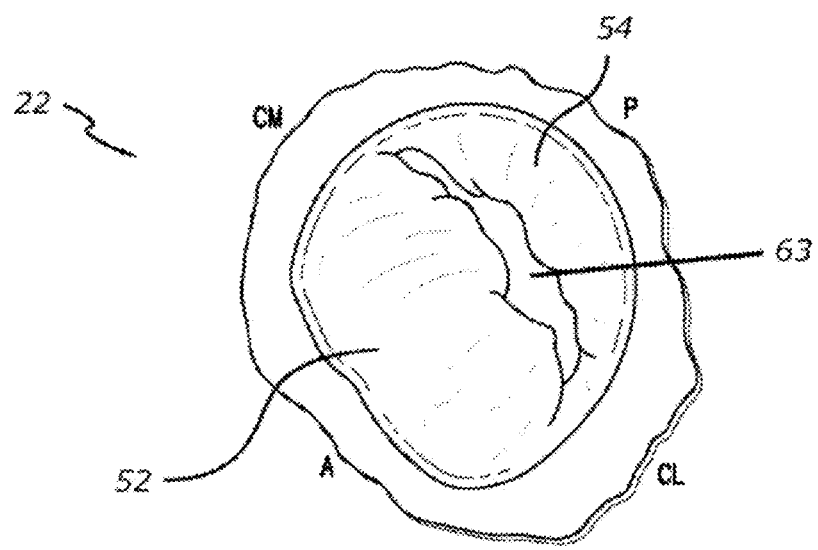
FIG. 2 is a top perspective view of a dysfunctional mitral valve with a visible gap between the mitral leaflets.

FIG. 2 illustrates a prolapsed mitral valve 22. As can be seen with reference to FIG. 2, prolapse occurs when a leaflet 52, 54 of the mitral valve 22 is displaced into the left atrium (not shown) during systole. Because one or more of the leaflets 52, 54 malfunction, the mitral valve 22 does not close properly, and, therefore, the leaflets 52, 54 fail to coapt. This failure to coapt causes a gap 63 between the leaflets 52, 54 that allows blood to flow back into the left atrium, during systole, while it is being ejected into the left ventricle. As set forth above, there are several different ways a leaflet may malfunction, which can thereby lead to regurgitation.

Mitral valve regurgitation increases the workload on the heart and may lead to very serious conditions if left untreated, such as endocarditis, congestive heart failure, permanent heart damage, cardiac arrest, and ultimately death. Since the left heart is primarily responsible for circulating the flow of blood throughout the body, malfunction of the mitral valve 22 is particularly problematic and often life threatening.

As described in detail in PCT International Application No. PCT/US2012/043761 (published as WO 2013/003228 A1) (referred to herein as "the '761 PCT Application), the entire disclosure of which is incorporated herein by reference, methods and devices are provided for performing non-invasive procedures to repair a cardiac valve, such as a mitral valve. Such procedures include procedures to repair regurgitation that occurs when the leaflets of the mitral valve do not coapt at peak contraction pressures, resulting in an undesired back flow of blood from the ventricle into the atrium. As described in the '761 PCT Application, after the malfunctioning cardiac valve has been assessed and the source of the malfunction verified, a corrective procedure can be performed. Various procedures can be performed in accordance with the methods described therein to effectuate a cardiac valve repair, which will depend on the specific abnormality and the tissues involved.

In some embodiments, a method includes the implantation of one or more artificial chordae tendineae into one or more leaflets of a malfunctioning mitral valve 22 and/or tricuspid valve. It is to be noted that, although the following procedures are described with reference to repairing a cardiac mitral valve by the implantation of one or more artificial chordae, the methods presented are readily adaptable for various types of leaflet repair procedures. In general, the methods herein will be described with reference to a mitral valve 22.

Figure 3:
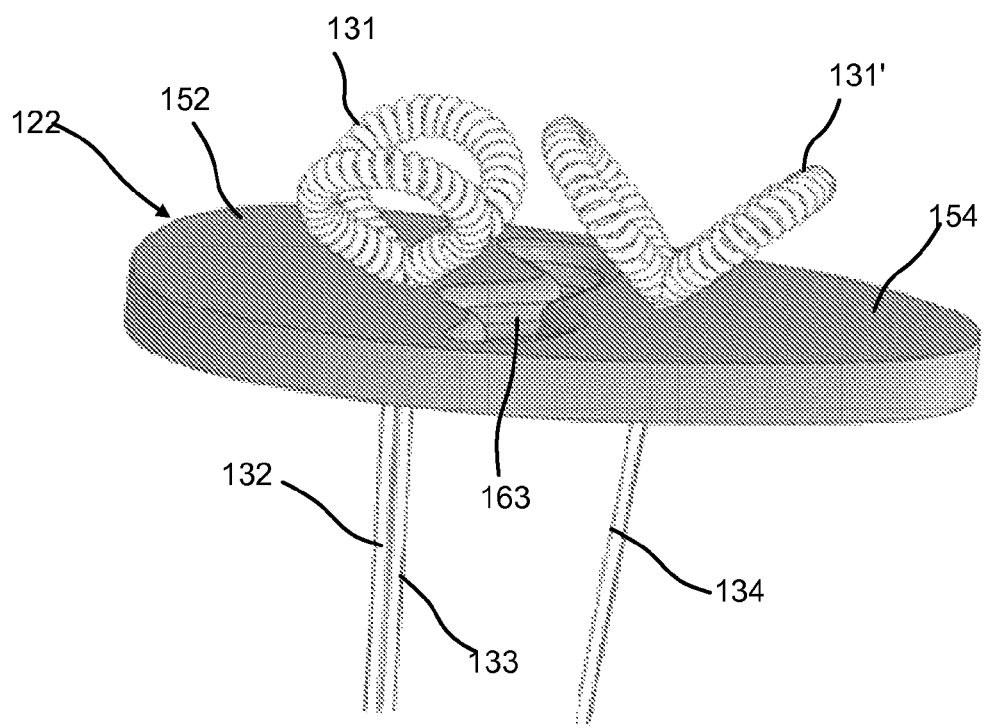
FIG. 3 is a schematic illustration of a side perspective view of a mitral valve with implants, according to an embodiment.

FIGS. 3-12 illustrate a method and device for securing an artificial tendineae that has been implanted as described in the '761 PCT Application. FIG. 3 is a schematic illustration of a mitral valve 122 with leaflets 152, 154 that are separated by a gap 163. As shown in FIG. 3, two bulky knot implants 131, 131' are disposed on an atrial, distal, or top side of the leaflets 152, 154, respectively. The implants 131, 131' can be formed with a suture material that forms a loop on the atrial side of the leaflets 152, 154 and extends through the leaflets 152, 154, with two loose suture end portions that extend on the ventricular, proximal, or bottom side of the leaflets 152, 154. The implant 131 has suture end portions 132 and 133, and the implant 131' has suture end portions 134 and 135 (not shown in FIG. 3; see FIG. 5).

Figure 4:
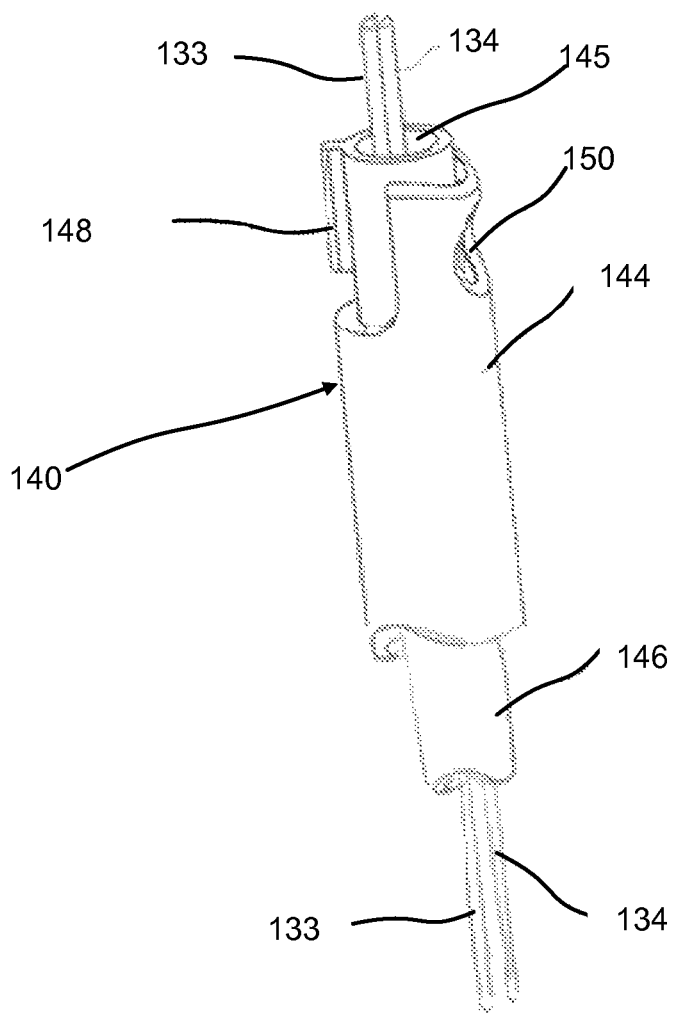
FIG. 4 is a side view of a portion of a knot pusher device, according to an embodiment.

After the implants 131, 131' are in a desired position, for example, as confirmed with imaging, a securing device 140 as shown in FIG. 4 can be used during a procedure to secure the implants 131, 131' in the desired position and to secure the valve leaflets 152, 154 in an edge-to-edge relationship. For example, the implants 131, 131' can be secured together to decrease the septal-lateral distance of the mitral valve annulus. The securing device 140 includes an outer member 144 and an inner member 146 movably disposed within a lumen of the outer member 144. The outer member 144 defines a side window 150 through which a portion of a suture can be disposed as described in more detail below. The inner member 146 defines a lumen 145 and includes a stop member 148. The stop member 148 can be used to limit the movement of the outer tubular member 144 along the length of the inner member 146. The lumen 145 can receive one or more suture portions as described in more detail below.

The inner member 146 can be used to hold a suture portion extending from the knot implant 131 and a suture portion extending from the knot implant 131'. For example, FIG. 4 illustrates the suture portion 133 from implant 131 and the suture portion 134 from implant 131' extending through the lumen 145. The outer member 144 can be used to tie knots in the other two free end suture portions, for example, the suture portion 132 from implant 131 and suture portion 135 from implant 131'. Although not shown, the inner member 146 can also include a clamp portion or member that can be used to clamp or hold the suture portions during the procedure.

Figure 5:
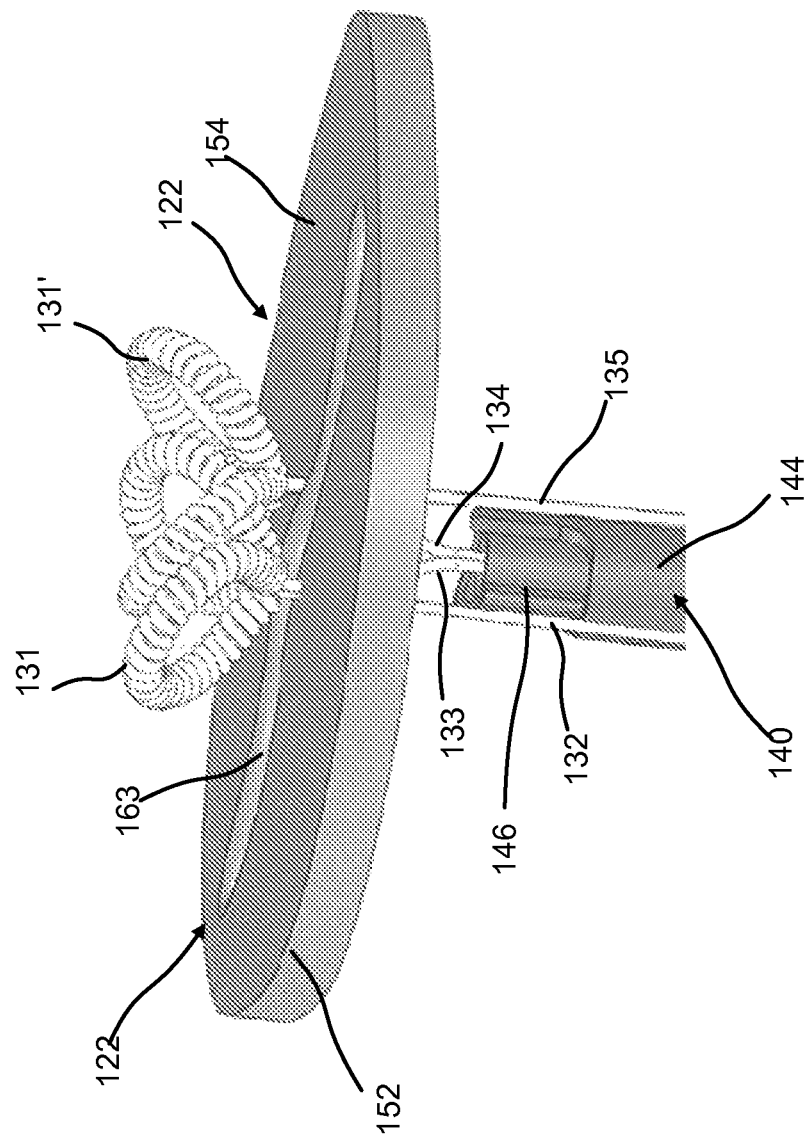
FIG. 5 is a schematic illustration of a side perspective view of the mitral valve of FIG. 3, shown with a portion of the knot pusher device of FIG. 4 in a first position of a procedure to repair a mitral valve.
Figure 6:
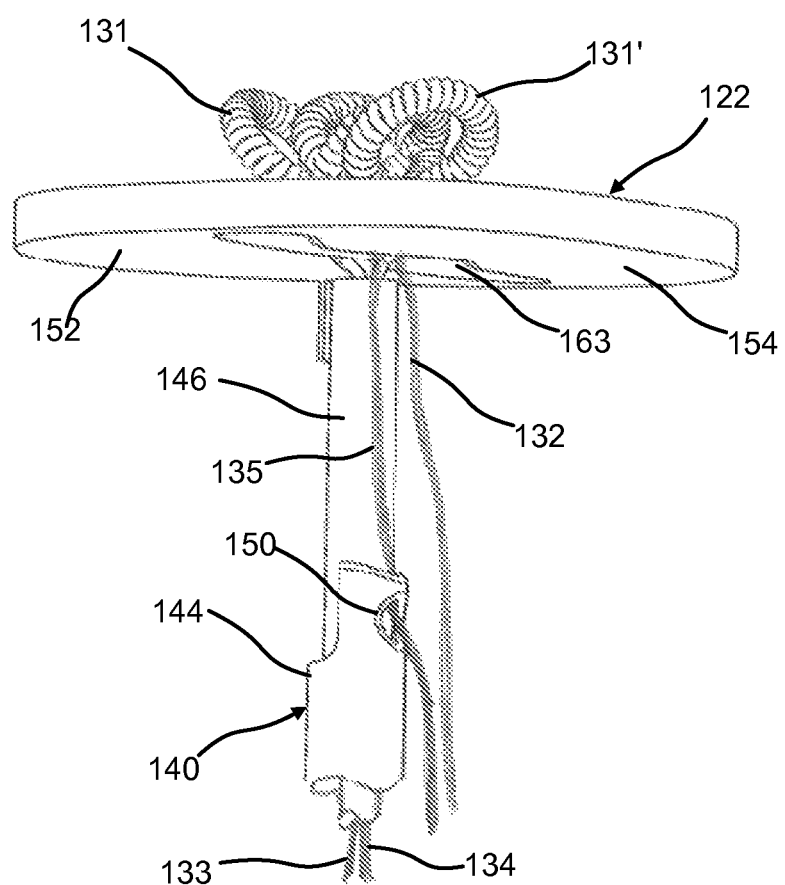
FIG. 6 is a schematic illustration of a bottom perspective view of the mitral valve of FIG. 3, shown with a portion of the knot pusher device of FIG. 4 in a second position of a procedure to repair a mitral valve.
Figure 7:
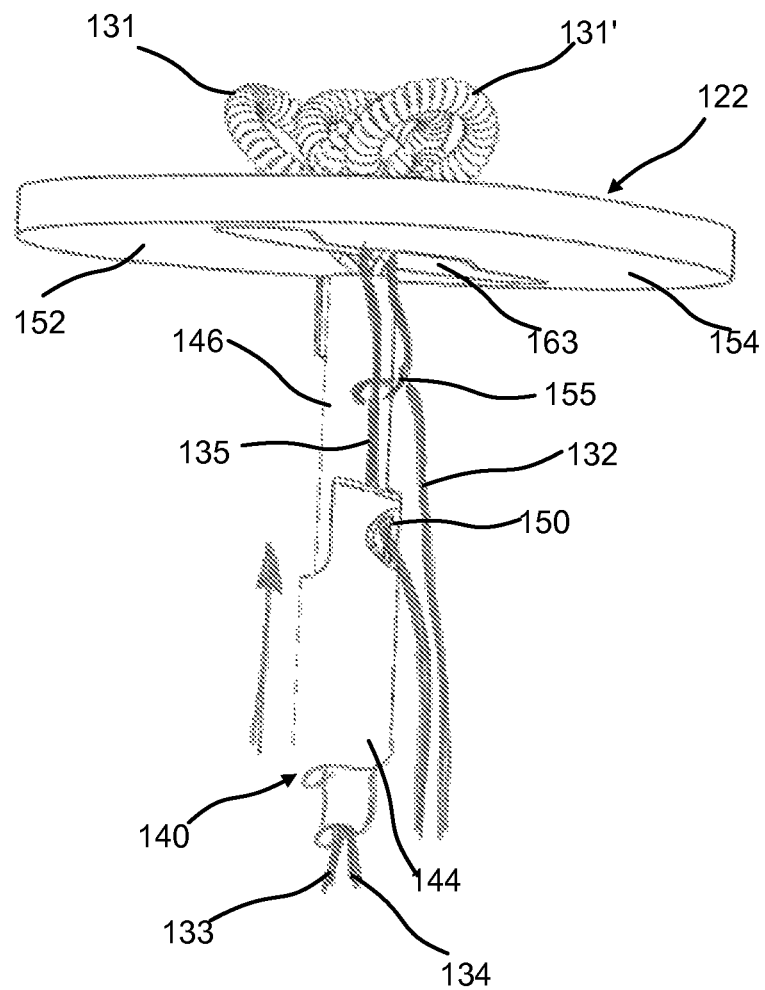
FIG. 7 is a schematic illustration of a bottom perspective view of the mitral valve of FIG. 3, shown with a portion of the knot pusher device of FIG. 4 in a third position of a procedure to repair a mitral valve.
Figure 8:
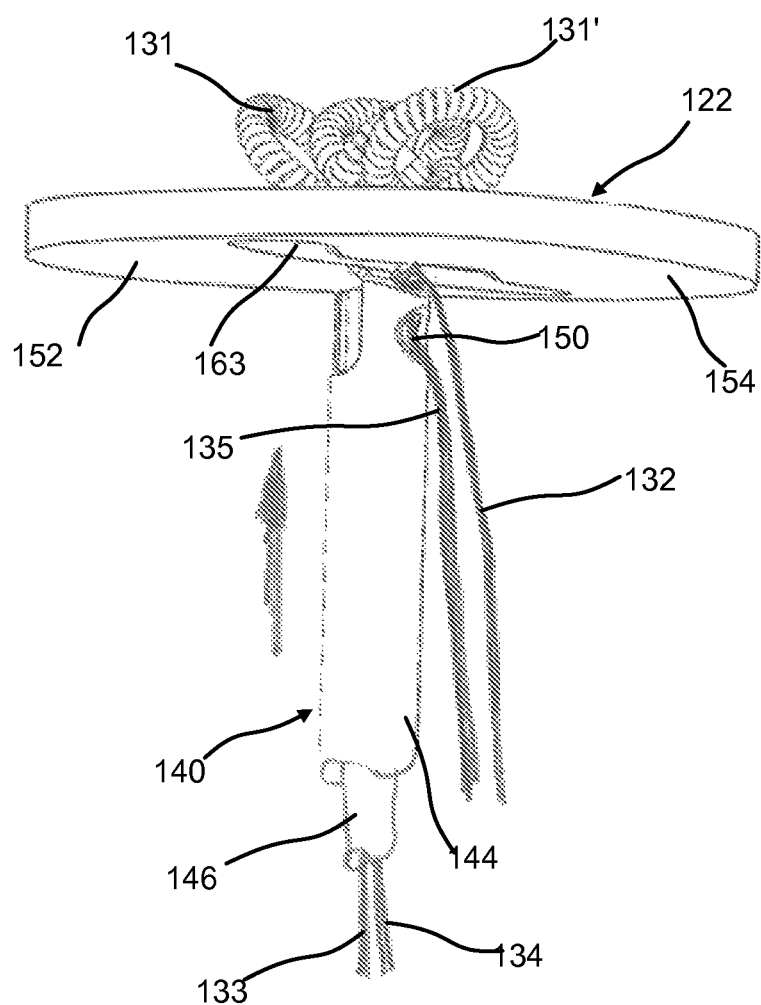
FIG. 8 is a schematic illustration of a bottom perspective view of the mitral valve of FIG. 3, shown with a portion of the knot pusher device of FIG. 4 in a fourth position of a procedure to repair a mitral valve.

During a procedure to repair a mitral valve, the suture portion 133 of the implant 131 and the suture portion 134 of the implant 131' are threaded through the lumen 145 of the inner member 146 as shown in FIGS. 4 and 5. The two other free end suture portions 132 and 135 extend along an outer portion of the outer member 144. The inner member 146 can be moved relative to the outer member 144 distally toward the leaflets 152, 154 until a distal end of the inner member 146 contacts the bottom side of the leaflets 152, 154 (or any other position the operator deems appropriate) and can clamp or maintain the sutures temporarily in place, such as by applying and maintaining tension on the sutures to minimize the force that the moving leaflets 152, 154 exert on the two other free end suture portions 132 and 135. The suture portion 135 can be threaded through a distal opening of the outer member 144 and through the side window 150 as shown in FIG. 6. A half hitch knot 155 can then be formed with the suture portion 132 and the suture portion 135 distal of the distal end of the outer member 144, as shown in FIG. 7.

Figure 9:
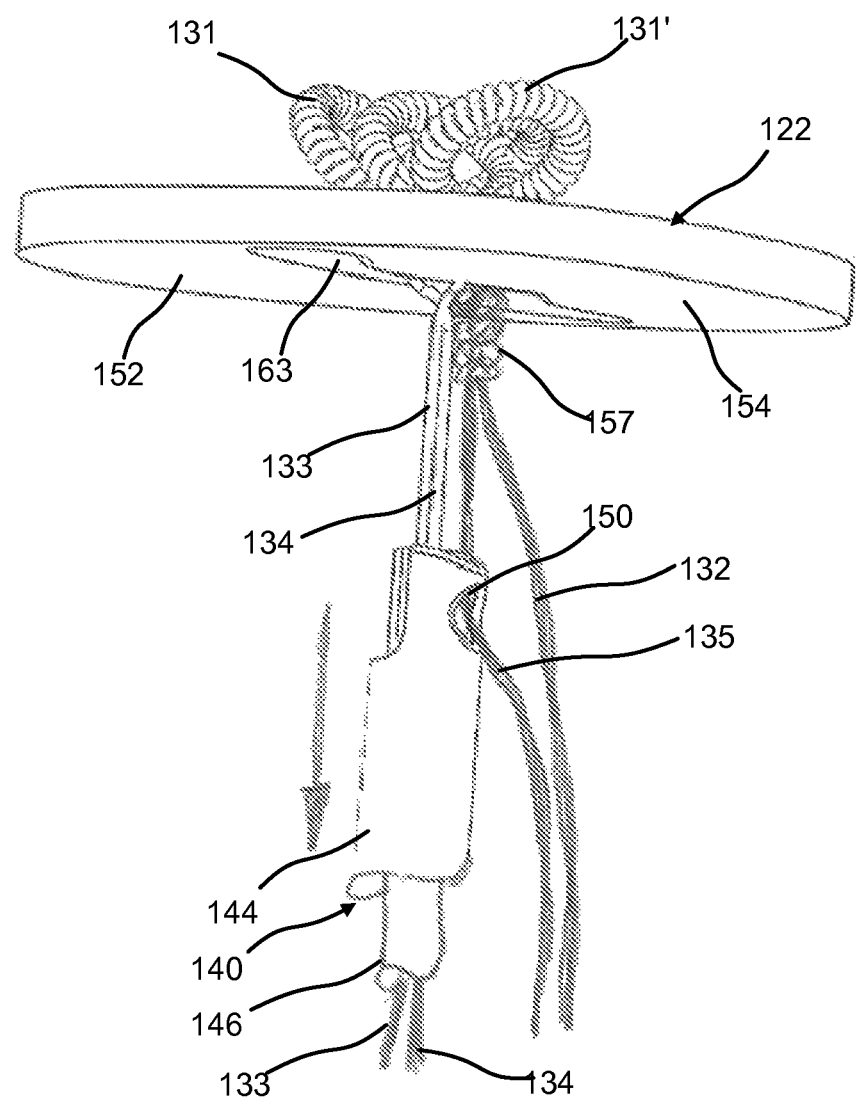
FIG. 9 is a schematic illustration of a bottom perspective view of the mitral valve of FIG. 3, shown with a portion of the knot pusher device of FIG. 4 in a fifth position of a procedure to repair a mitral valve.

After the half hitch knot has been formed, the outer member 144 can be moved distally to push the half hitch knot 155 distally until it contacts or is near the ventricular side of the leaflets 152, 154 as shown in 8. This process of tying half hitch knots and moving them distally toward the leaflets is repeated until a desired number of knots are formed and a stack or sequence of knots 157 is formed, as shown in FIG. 9. In some embodiments, it may be desirable to have at least two half hitch knots to secure the implants 131, 131'. The movement of the leaflets (during normal functioning) does not affect the knot tying process because the inner member 146 acts as a temporary fixation device. After the desired number of knots have been secured, the securing device 140 can be removed by moving the securing device 140 proximally, as shown in FIG. 9. This releases the hold on the suture portions 133 and 134. Half hitch knots can now be formed with the suture portions 133 and 134.

Figure 10:
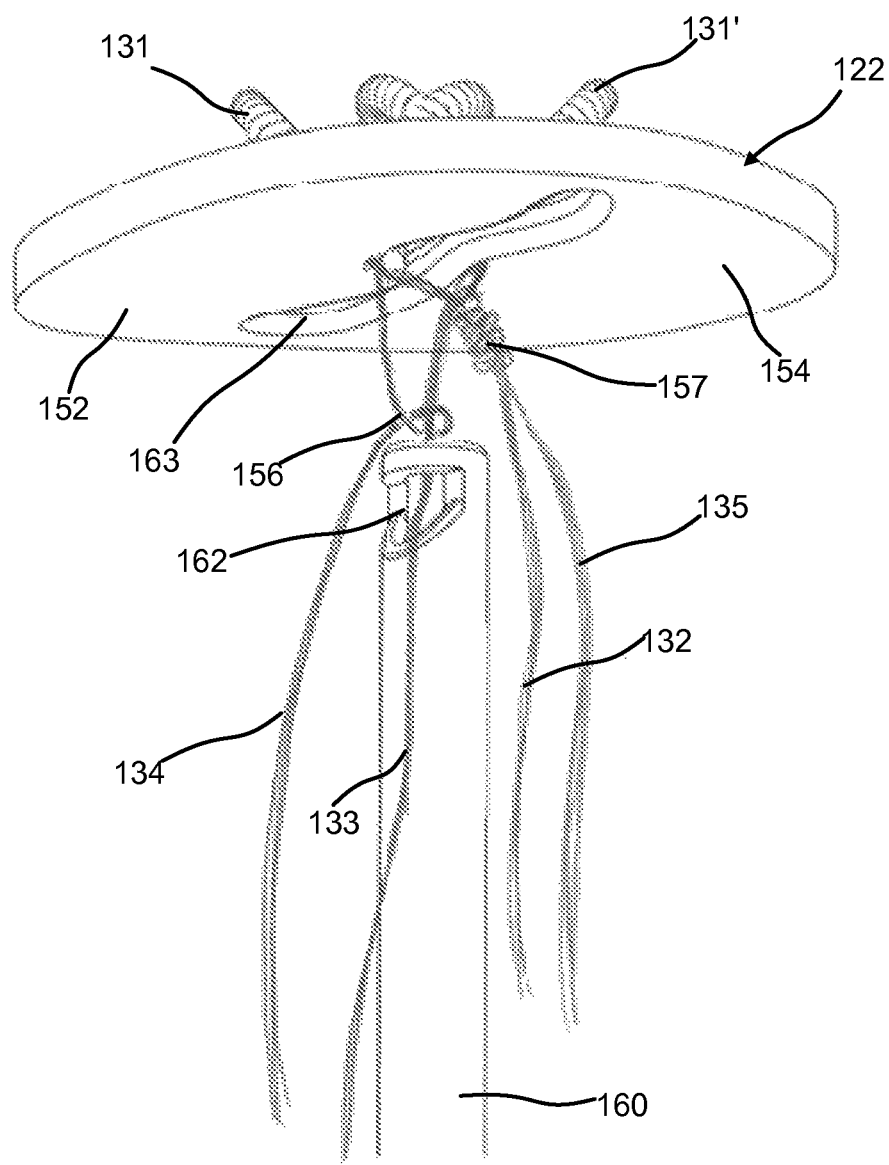
FIG. 10 is a schematic illustration of a bottom perspective view of the mitral valve of FIG. 3, shown with a portion of the knot pusher device of FIG. 4 in a sixth position of a procedure to repair a mitral valve.
Figure 11:
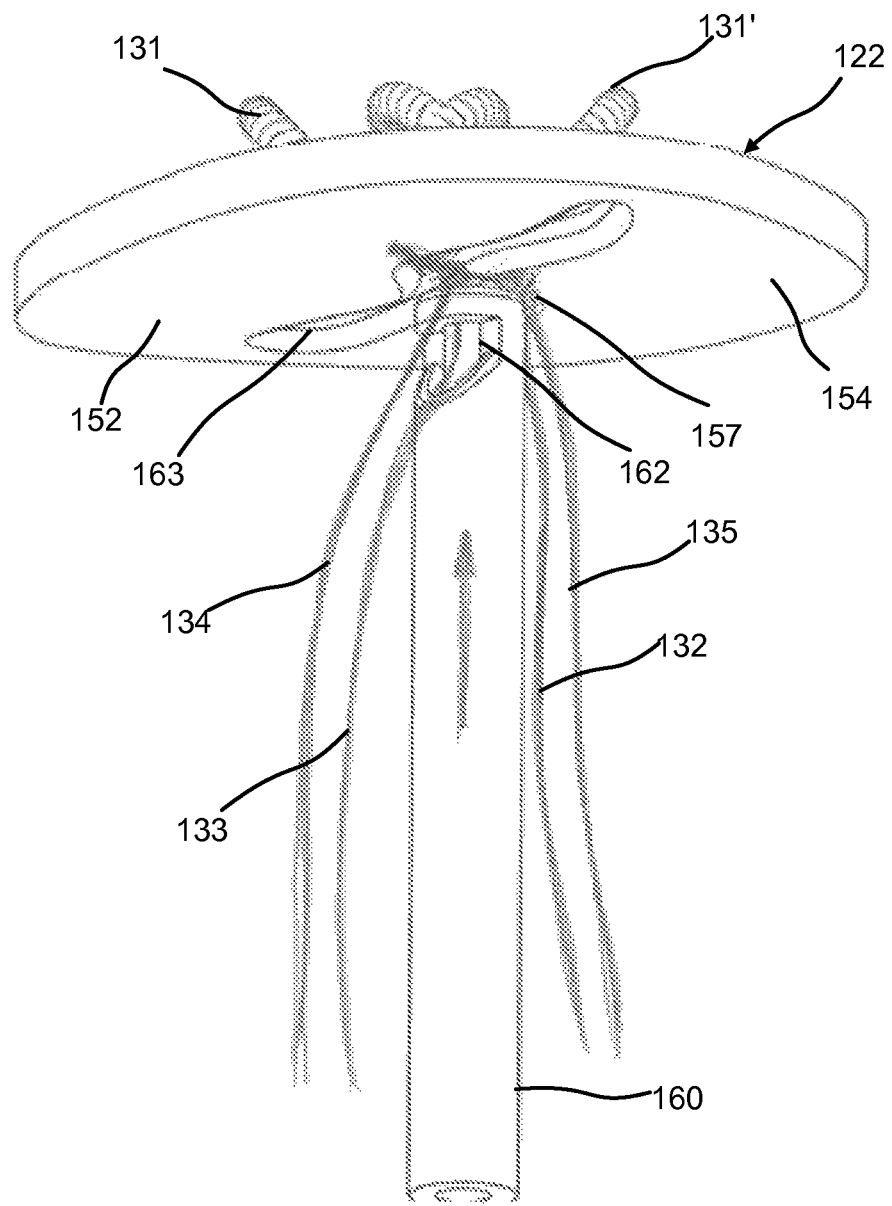
FIG. 11 is a schematic illustration of a bottom perspective view of the mitral valve of FIG. 3, shown with a portion of the knot pusher device of FIG. 4 in a seventh position of a procedure to repair a mitral valve.

To form the half hitch knots on the suture portions 133 and 134, the outer member 144 of the securing device 140 can be used, or a separate, single lumen pushing device 160, as shown in FIG. 10, can be used. As shown in FIG. 10, the suture portion 133 can be threaded through a distal end opening defined by the pushing device 160 and then inserted through a side window 162 defined by the pushing device 160. A half hitch knot 156 can then be formed with the suture portion 133 and suture portion 134 as shown in FIG. 10. The pusher device 160 can be moved distally to push the half hitch knot 156 distally toward the bottom side of the leaflets 152, 154, as shown in FIG. 11. As with the suture portions 132 and 135, multiple half hitch knots 156 can be formed with suture portions 133 and 134 and moved distally to form a stack or sequence of knots 159. The pusher device 160 can then be removed.

Figure 12:
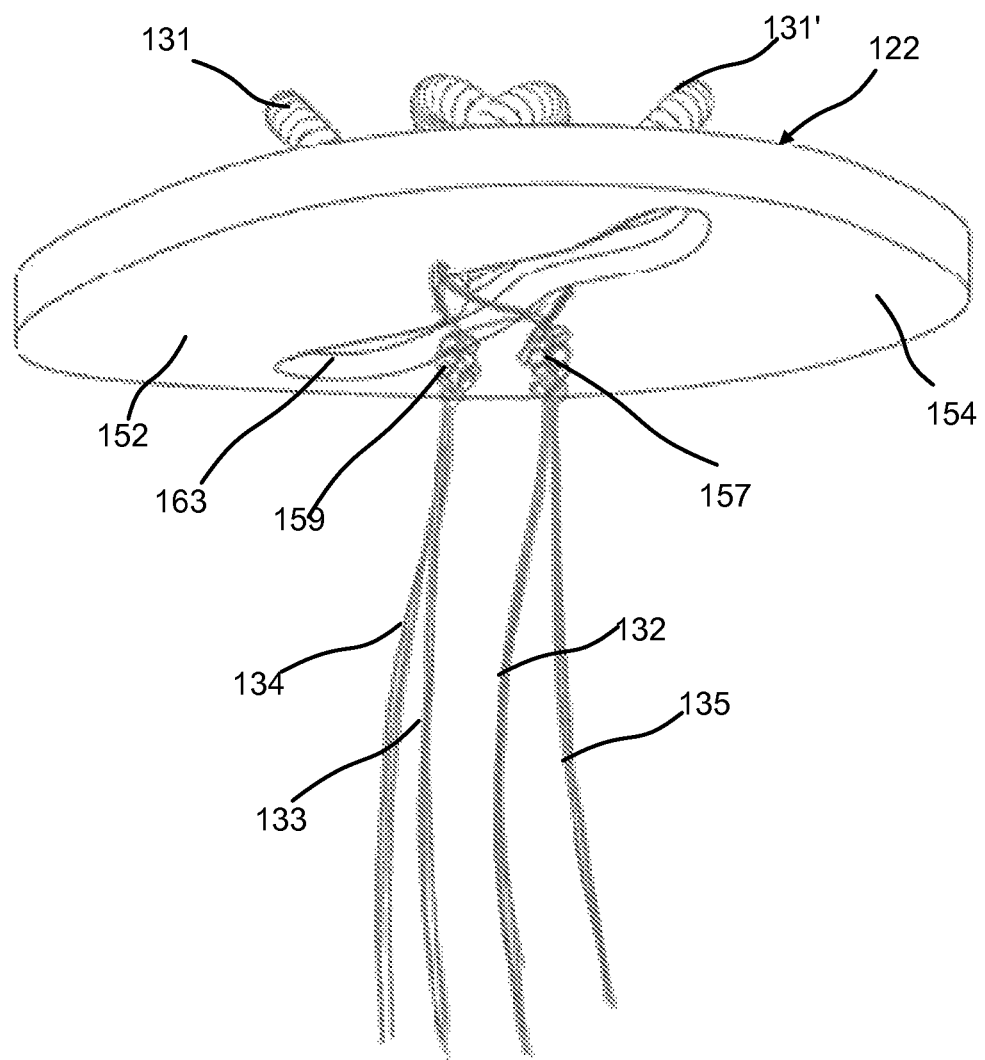
FIG. 12 is a schematic illustration of a bottom perspective view of the mitral valve of FIG. 3, shown after the knot pusher device of FIG. 4 has been removed from the implants, i.e. in an eighth position of a procedure to repair a mitral valve.

FIG. 12 illustrates the leaflets 152, 154 and the stack of knots 157 formed with suture portions 132 and 135 and the stack of knots 159 formed with suture portions 133 and 134. Such knots are referred to as an edge-to-edge repair or an Alfieri stitch or procedure. After the desired number of half hitch knots have been formed with all four of the suture end portions 132, 133, 134 and 135, the ends of the sutures can be cut or snipped to a desired length. Alternatively, the distal portion of the suture ends can be secured at or near the apex of the left ventricle to add a downward force on the stack of knots 157, 159 as described in more detail below.

FIGS. 13 and 14 each illustrate a different embodiment of a pusher device that can be used in a mitral valve repair procedure as described herein. The pusher device 260 shown in FIG. 13 is a single knot pusher device and pusher device 360 shown in FIG. 14 is a double knot pusher device. Pusher device 260 includes a prong 264 and the pusher device 360 includes two prongs 364. Each of the pusher devices 260 and 360 can be used to push a half hitch knot distally toward the bottom side of the mitral valve leaflets. The pusher device 360 can be used to push two half hitch knots simultaneously. For example, the pusher devices 260, 360 can be used in conjunction with another device that can be used to hold two free end portions of suture extending from an implant such as the implants 131, 131'. A half hitch knot can be formed with the other two free end portions of suture and the pusher device 260 or 360 can be used to push the half hitch knot distally to a desired position below the leaflets of the valve. For example, the prong 264 of the pusher device 260 can push the half hitch knot distally. With the pusher device 360, two half hitch knots can be formed and the two prongs 364 can each be used to push one of the half hitch knots distally to the desired position. When in the desired position, the prongs 364 can be removed from the half hitch knots and the two half hitch knots can be tightened onto one another before pushing additional half hitch knots to the initial stack of two knots. Either of these pusher devices can be used in conjunction with any suitable device or technique to approximate and maintain the edges of the valve leaflets while the first two or more knots, e.g. half hitches, are moved to the desired position adjacent the ventricular side of the leaflets using the pusher device. For example, a tube such as the inner member 146 of the securing device 140 can be used. Alternatively, rapid pacing of the heart can be used to minimize the relative motion of the edges of the valve leaflets while knots are placed and secured. Once a suture portion from each of at least one implant on each leaflet have been knotted together, the leaflets are secure in the desired edge-to-edge relationship, and additional suture portions of the same, and/or additional, implants can be knotted together.

In some embodiments, in addition to securing the mitral valve implants (e.g., 131, 131') with half hitch knots, or alternatively, it may be desirable to include a holding member to anchor the free, proximal ends of the suture portions. Examples of such anchoring devices are shown and described in the '761 PCT Application with reference to FIG. 21. There, the suture ends are anchored outside the apex of the ventricle by tying knots or using a pledget as shown in FIG. 21.

Figure 15:
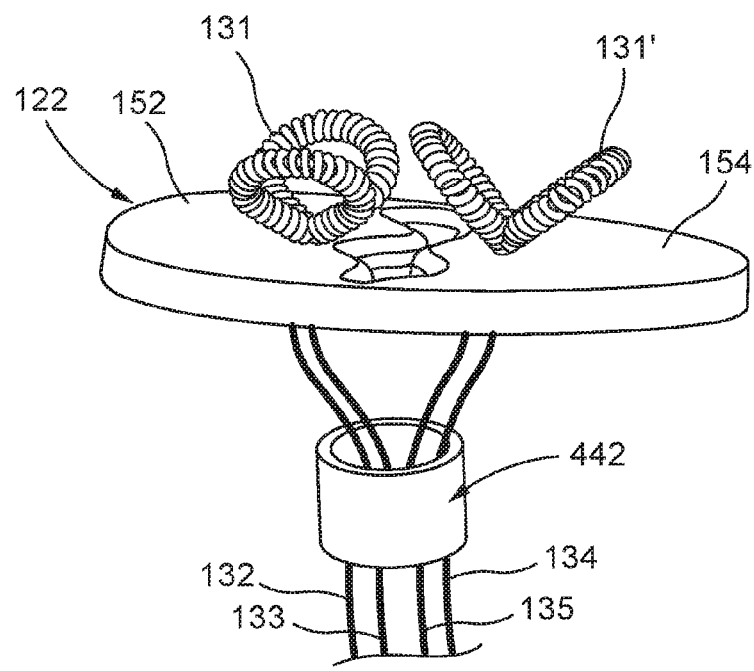
FIG. 15 is a schematic illustration of a side perspective view of the mitral valve of FIG. 3, illustrating a collar coupled to the suture portions, according to an embodiment.

In another embodiment, after implanting one or more bulky knot implants in each mitral valve leaflet, the terminal ends of all of the suture portions can be drawn through a tubular collar 442, as shown in FIG. 15. Tubular collar 442 may be formed of any suitable material such as ePTFE. The terminal ends can be drawn into and through the tubular collar 442 using any suitable technique, such as inserting a conventional suture threading device with an eyelet at its distal end through the tubular collar 442, capturing the terminal ends, and then withdrawing the suture threader and the terminal ends proximally through the tubular collar 442. The tubular collar 442 can be disposed in the desired position proximate to the ventricular side of the leaflets, and tension applied to at least one terminal end of each implant, thus approximating the leaflet edges. Tubular collar 442 and terminal ends of the implants can then be secured in position in any of several ways. For example, if the lumen of the tubular collar 442 is sufficiently small in comparison to the perimeter of the bundled terminal ends, knots, e.g. half hitches, can be formed in the terminal ends and pushed up against the proximal end of tubular collar 442, using any of the techniques described above. Alternatively, one or more terminal ends of each implant can be passed distally along the outside of tubular collar 442, then proximally through the lumen of tubular collar 442, and knotted to each other. The remainder of the terminal ends can then be clipped off proximally to the knots, or can be secured to the ventricular apex, as discussed above.

In some embodiments, the suture portions from one of the implants can be threaded through a tubular collar and the suture portions for the other implant can be used to tie half hitches to hold the collar in position. For example, the suture portions 133 and 134 can be threaded through the lumen of the collar 442, and the suture portions 132 and 135 can extend outside the collar 442. A half hitch can then be tied between, for example, suture portion 132 and suture portion 133, and a half hitch can be tied between suture portion 135 and suture 134, to hold the collar in place. In other words, half hitches are tied between a suture portion of one of the implants 131, 131' and a suture portion of the other of the implants 131, 131'.

Figure 16:
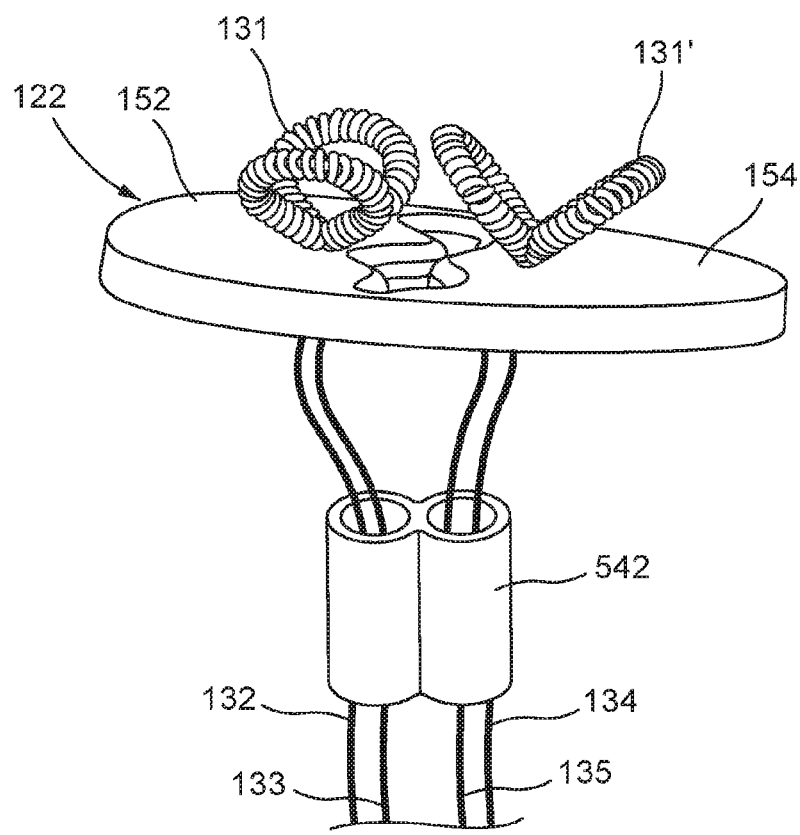
FIG. 16 is a schematic illustration of a side perspective view of the mitral valve of FIG. 3, illustrating a collar coupled to the suture portions, according to another embodiment.

In another embodiment, after implanting one or more bulky knot implants in each mitral valve leaflet, the terminal ends of the suture portions of the bulky knot implants can be drawn through a two-lumen collar 542, as shown in FIG. 16. The two-lumen collar 542 can be disposed in the desired position proximate to the ventricular side of the leaflets, and tension applied to at least one terminal end of each implant, thus approximating the leaflet edges. Two-lumen collar 542 and terminal ends of the implants can then be secured in position in any of several ways. For example, a terminal end from each of the two lumens can be knotted together and the knot(s) pushed against the proximal end of the two-lumen collar, e.g. against the land between the two lumens. The remaining terminal ends can be similarly knotted. The terminal ends of the two or more implants in the leaflets can be disposed through the two lumens in any desired combination, e.g. one terminal end of each implant through one lumen, and the other terminal end of each implant through the other lumen, or both terminal ends of one implant through one lumen and both terminal ends of the other (or every other) implant through the other lumen. The remainder of the terminal ends can then be clipped off proximally to the knots, or can be secured to the ventricular apex, as discussed above. Alternatively, the collar can have three or more lumens.

In alternatives to either of the two preceding embodiments, rather than being formed as a collar, the single- or two-lumen device can be formed as an elongate tube that is sufficiently long to extend from the mitral valve to, or through, the ventricular apex, and the tube and terminal ends of the implants can be secured at the apex using any suitable technique.

The above-described procedures can be performed manually, e.g., by a physician, or can alternatively be performed fully or in part with robotic assistance. In addition, although some embodiments described herein include the use of a collar to secure the terminal ends of the suture portions, it should be understood that any of the embodiments described herein can use such a collar in addition to, or alternatively to using half hitch knots. Further, although not specifically described for some embodiments, in various embodiments, the heart may receive rapid pacing to minimize the relative motion of the edges of the valve leaflets while knots are placed and secured.

While various embodiments have been described above, it should be understood that they have been presented by way of example only, and not limitation. Where methods described above indicate certain events occurring in certain order, the ordering of certain events may be modified.

Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

What is claimed is:

1. A method, comprising:
    disposing on an atrial side of a first leaflet of a mitral valve a first implant, the first implant including a first loop portion, a first suture portion extending from the first loop portion proximally through the first leaflet to the ventricular side of the first leaflet and a second suture portion extending from the first loop portion proximally through the first leaflet to the ventricular side of the first leaflet;
    disposing on an atrial side of a second leaflet of the mitral valve a second implant, the second implant including a second loop portion, a third suture portion extending from the second loop portion proximally through the second leaflet to the ventricular side of the second leaflet and a fourth suture portion extending from the second loop portion proximally through the second leaflet to the ventricular side of the second leaflet;
    placing the first suture portion within a lumen of an inner member of a securing device;
    placing the third suture portion within the lumen of the inner member of the securing device;
    inserting one of the second suture portion and the fourth suture portion through a distal opening defined by an outer member of the securing device and through a side opening defined by the outer member;
    forming a knot with the second suture portion and the fourth suture portion outside the securing device; and
    moving the knot distally toward the ventricular side of the mitral valve using the outer member of the securing device.

2. The method of claim 1, wherein the knot is a first knot, the method further comprising:
    after moving the first knot, forming a second knot with the second suture portion and the fourth suture portion outside the securing device; and
    moving the second knot distally toward the ventricular side of the mitral valve and toward the first knot using the outer member of the securing device.

3. The method of claim 2, further comprising:
    after moving the second knot, removing the first suture portion and the third suture portion from the lumen of the inner member of the securing device;
    inserting one of the first suture portion and the third suture portion through the distal opening of the outer member of the securing device and through the side opening of the outer member;
    forming a third knot with the first suture portion and the third suture portion outside the securing device; and
    moving the third knot distally toward the ventricular side of the mitral valve using the outer member of the securing device.

4. The method of claim 3, further comprising:
    after moving the third knot, forming a fourth knot with the first suture portion and the third suture portion outside the securing device; and
    moving the fourth knot distally toward the ventricular side of the mitral valve and toward the third knot using the outer member of the securing device.

5. The method of claim 4, further comprising:
    after moving the fourth knot, securing at least one of collectively the first suture portion and the third suture portion or collectively the second suture portion and the fourth suture portion to a portion of a ventricular wall to provide a downward force on at least one of the first knot, the second knot, the third knot or the fourth knot.

6. The method of claim 2, further comprising:
    after moving the second knot, removing the first suture portion and the third suture portion from the lumen of the inner member of the securing device;
    inserting one of the first suture portion and the third suture portion through a distal opening defined by a pusher device and through a side opening defined by the pusher device;
    forming a third knot with the first suture portion and the third suture portion outside the pusher device; and
    moving the third knot distally toward the ventricular side of the mitral valve using the pusher device.

7. The method of claim 1, wherein the knot is a first knot, the method further comprising:
    after moving the first knot, removing the first suture portion and the third suture portion from the lumen of the inner member of the securing device;
    inserting one of the first suture portion and the third suture portion through the distal opening of the outer member of the securing device and through the side opening of the outer member;
    forming a second knot with the first suture portion and the third suture portion outside the securing device; and
    moving the second knot distally toward the ventricular side of the mitral valve using the outer member of the securing device.

8. The method of claim 1, further comprising:
    prior to inserting one of the second suture portion and the fourth suture portion through the distal opening of the outer member of the securing device and through the side opening of the outer member, moving the outer member proximally relative to the inner member.

9. The method of claim 1, wherein moving the knot toward the ventricular side of the mitral valve using the outer member of the securing device includes moving the outer member distally relative to the inner member.

10. The method of claim 1, wherein the knot is a first knot, the method further comprising:
    after moving the first knot, removing the first suture portion and the third suture portion from the lumen of the inner member of the securing device;
    inserting one of the first suture portion and the third suture portion through a distal opening defined by a pusher device and through a side opening defined by the pusher device;
    forming a second knot with the first suture portion and the third suture portion outside the pusher device; and
    moving the second knot distally toward the ventricular side of the mitral valve using the pusher device.

11. The method of claim 1, wherein the forming the knot with the second suture portion and the fourth suture portion includes forming a half hitch knot.

12. A method, comprising:
disposing on an atrial side of a first leaflet of a mitral valve a first implant, the first implant including a first loop portion, a first suture portion extending from the first loop portion proximally through the first leaflet to the ventricular side of the first leaflet and a second suture portion extending from the first loop portion proximally through the first leaflet to the ventricular side of the first leaflet;
disposing on an atrial side of a second leaflet of the mitral valve a second implant, the second implant including a second loop portion, a third suture portion extending from the second loop portion proximally through the second leaflet to the ventricular side of the second leaflet and a fourth suture portion extending from the second loop portion proximally through the second leaflet to the ventricular side of the second leaflet;
forming a first knot with the first suture portion and the third suture portion;
moving the first knot distally toward the ventricular side of the mitral valve using a pusher device;
forming a second knot with the second suture portion and the fourth suture portion; and
moving the second knot distally toward the ventricular side of the mitral valve using the pusher device, the first knot and the second knot configured to secure the first implant and the second implant together to decrease the septal-lateral distance of the mitral valve annulus.

13. The method of claim 12, further comprising:
prior to forming the second knot, forming a third knot with the first suture portion and the third suture portion; and
moving the third knot distally toward the ventricular side of the mitral valve using the pusher device.

14. The method of claim 13, further comprising:
after forming the second knot, forming a fourth knot with the second suture portion and the fourth suture portion; and
moving the fourth knot distally toward the ventricular side of the mitral valve using the pusher device.

15. The method of claim 14, further comprising:
after moving the fourth knot, securing at least one of collectively the first suture portion and the third suture portion or collectively the second suture portion and the fourth suture portion to a portion of a ventricular wall to provide a downward force on at least one of the first knot, the second knot, the third knot or the fourth knot.

16. The method of claim 14, wherein the forming the first knot and the forming the second knot each include forming a half hitch knot.

* * * * *